(12) United States Patent
Rho et al.

(10) Patent No.: US 7,485,750 B2
(45) Date of Patent: Feb. 3, 2009

(54) HYDROXAMIC ACID DERIVATIVES AND THE PREPARATION METHOD THEREOF

(75) Inventors: Ho Sik Rho, Yongin-si (KR); Heung Soo Baek, Anyang-si (KR); Jeong A. Lee, Yongin-si (KR); Chang Man Park, Seoul (KR); Duck Hoo Kim, Seoul (KR); Ih Soop Chang, Yongin-si (KR); Ok Sub Lee, Anyang-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 11/919,131

(22) PCT Filed: Mar. 21, 2006

(86) PCT No.: PCT/KR2006/001019

§ 371 (c)(1),
(2), (4) Date: Dec. 17, 2007

(87) PCT Pub. No.: WO2006/118380

PCT Pub. Date: Nov. 9, 2006

(65) Prior Publication Data

US 2008/0242730 A1 Oct. 2, 2008

(30) Foreign Application Priority Data

Apr. 29, 2005 (KR) .................... 10-2005-0035986

(51) Int. Cl.
*C07C 259/04* (2006.01)
*A61K 31/19* (2006.01)
(52) U.S. Cl. .................... 562/621; 562/622; 514/575
(58) Field of Classification Search .................... None
See application file for complete search history.

(56) References Cited

U.S. PATENT DOCUMENTS

| 5,128,479 | A | 7/1992 | Janssen et al. |
| 5,700,811 | A | 12/1997 | Breslow et al. |
| 7,282,522 | B2 * | 10/2007 | Rho et al. .................... 514/575 |
| 2002/0172967 | A1 | 11/2002 | Gadek et al. |

FOREIGN PATENT DOCUMENTS

WO 2005/019162 3/2005

OTHER PUBLICATIONS

International Search Report dated Jul. 7, 2006.

* cited by examiner

*Primary Examiner*—Karl J Puttlitz
(74) *Attorney, Agent, or Firm*—Nixon & Vanderhye P.C.

(57) ABSTRACT

The present invention provides hydroxamic acid derivatives represented by the formula, having antioxidation, collagen biosynthesis promotion and skin pore contraction effects, and a method for preparation thereof. Further, the present invention provides skin-care external compositions for preventing skin aging, containing said hydroxamic acid derivatives represented by the formula as an active ingredient.

6 Claims, No Drawings

HYDROXAMIC ACID DERIVATIVES AND THE PREPARATION METHOD THEREOF

This application is the U.S. national phase of International Application No. PCT/KR2006/001019 filed 21 Mar. 2006 which designated the U.S. and claim priority to KR 10-2005-0035986 filed 29 Apr. 2005, the entire contents of each of which are hereby incorporated by reference.

FIELD OF THE INVENTION

The present invention relates to hydroxamic acid derivatives represented by the following formula (1), and to a method for the preparation thereof:

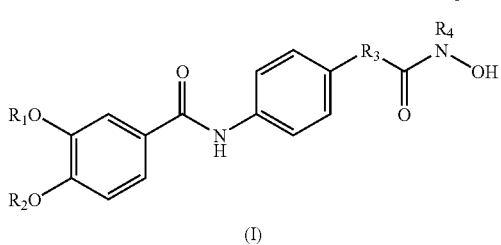

[Formula 1]

(I)

wherein, $R_1$ and $R_2$ are alkyl groups having from 1 to 10 carbon atoms;

$R_3$ is —$(CH)_n$—, wherein n=0 or 1; and $R_4$ is a hydrogen atom or methyl.

BACKGROUND OF THE INVENTION

Reactive oxygen species work as a cause material of skin aging. When skin is exposed to UV light, photochemical reactions continually occur at the skin so as to produce reactive oxygen species. These reactive oxygen species may damage skin cells or tissue. They destroy an antioxidant defence layer, consisting of antioxidant enzymes and non-enzymatic antioxidants, thereby shifting the balance of oxidants/antioxidants to the oxidative state. Such oxidative stress may lead to damage of living body components, such as lipid peroxidation, protein oxidation, activation of protease that destroys skin components, chain scission of collagen and elastin, which are elastic fibers, and abnormal cross conjugation thereof, chain scission of hyaluronic acid, promotion of melanin synthesis, and DNA oxidation. In addition, such damage of living body components may lead to various aging effects such as skin wrinkle formation, elasticity reduction and widening of skin pores. Although there have been many studies on skin aging such as skin wrinkle formation and skin elasticity reduction, few studies have been made of skin pores. However, the most important factor of skin pore widening is also oxidative stress.

The structural change of skin according to oxidative stress is that the thicknessess of the epidermis, dermis and subcutaneous are reduced. In addition, the ECM (extracellular matrix) of the dermis, which relates to elasticity and tensility of skin, is changed. The ECM consists of two components. One is elastic fiber, which comprises about 2-4% of the ECM, and the other is collagen, which comprises about 70-80% of the ECM. Under the influence of oxidative stress, collagen is decomposed so that collagen in the skin is reduced. As a person grows older, the ECM around skin pores is reduced; thereby skin pores widen.

Thus, the best solution to prevent the widening of skin pores is to inhibit oxidative stress, and the best solution to reduce the size of the widened skin pores is to increase the production of collagen around skin pores.

Although not directly related to the widening of skin pores, there have been many studies on antioxidants to inhibit oxidative stress, and many antioxidants have been actually developed, however, not all of them are effective for increasing collagen biosynthesis or reducing skin pore size.

Meanwhile, vitamin C and vitamin E are two antioxidants generally used. Vitamin C is a water soluble antioxidant, and vitamin E is a fat soluble antioxidant. Although these antioxidants show strong antioxidant effects, they can easily deteriorate when exposed to air, due to their instability. Thus, there is much limitation on their use. Another possible antioxidant is polyphenol. However, it also shows instability.

SUMMARY OF THE INVENTION

Under these circumstances, the present inventors conducted many studies in order to develop a novel compound showing antioxidant effects without showing instability, which is the problem of the prior developed antioxidant. As a result, a novel type of hydroxamic acid derivatives was synthesized. Furthermore, it was found that these hydroxamic acid derivatives have the same antioxidant effects as those of the vitamins (antioxidants) used until now. Based on these findings, the present invention was completed.

Therefore, an object of the invention is to provide novel hydroxamic acid derivatives, which have radical elimination ability as an antioxidant, collagen biosynthesis ability, and also an ability to inhibit the widening of skin pores due to oxidative stress, and to provide a method for preparing the same.

Hydroxamic acid is widely known as a metal chelator. Judging from the structural feature of hydroxamic acid, a hydroxy group of hydroxylamine adjacent to a carbonyl group forms chelation with metal cation.

In an additional feature, a hydroxy group of hydroxylamine can be easily converted into an anion, to be used in a similar manner to phenol. These structural features of hydroxamic acid were utilized to synthesize a novel anitioxidant having radical elimination ability and also a skin pore contraction effect.

The present invention relates to hydroxamic acid derivatives represented by the following formula (1):

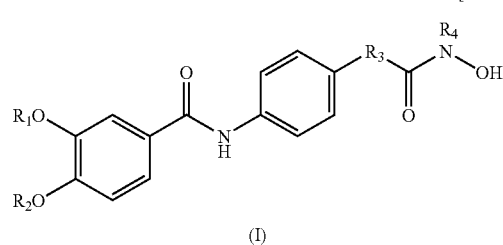

[Formula 1]

(I)

wherein, $R_1$ and $R_2$ is are alkyl group having from 1 to 10 carbon atoms;

$R_3$ is —(CH)n-, wherein n=0 or 1; and $R_4$ is a hydrogen atom or methyl.

Further, the present invention relates to a method for preparing the hydroxamic acid derivative represented by the above formula (1), which comprises the steps of:

1) Reacting 3,4-dialkoxy benzoic acid with methyl 4-aminobenzoate or 4-aminophenyl acetic acid methylester to produce a benzamide compound;

2) Hydrolyzing the methylester of the benzamide compound formed in step 1) to produce an acid; and 3) Reacting said acid with hydroxylamine hydrochloride or N-methyl hydroxylamine hydrochloride to produce a hydroxamic acid derivative.

Especially, in the last step of producing a hydroxamic acid derivative, one-step processing without protective/deprotective reactions is used to increase efficiency.

The present hydroxamic acid derivative may be prepared by the method below, comprising the steps of:

a) Converting 3,4-dialkoxy benzoic acid to anhydride by adding ethyl chloroformate thereto, and reacting the anhydride with methyl 4-aminobenzoate or 4-aminophenyl acetic acid methylester, to produce a benzamide compound;

b) Hydrolyzing methylester of benzamide compounds formed in step a), to produce an acid; and c) Converting the acid formed in step b) to anhydride by adding ethyl chloroformate thereto, and reacting said anhydride with hydroxylamine hydrochloride or N-methyl hydroxylamine hydrochloride, to produce a hydroxamic acid derivative.

The method of the present invention is described in more detail by the following reaction scheme. The method may be exemplified by the following reaction scheme 1:

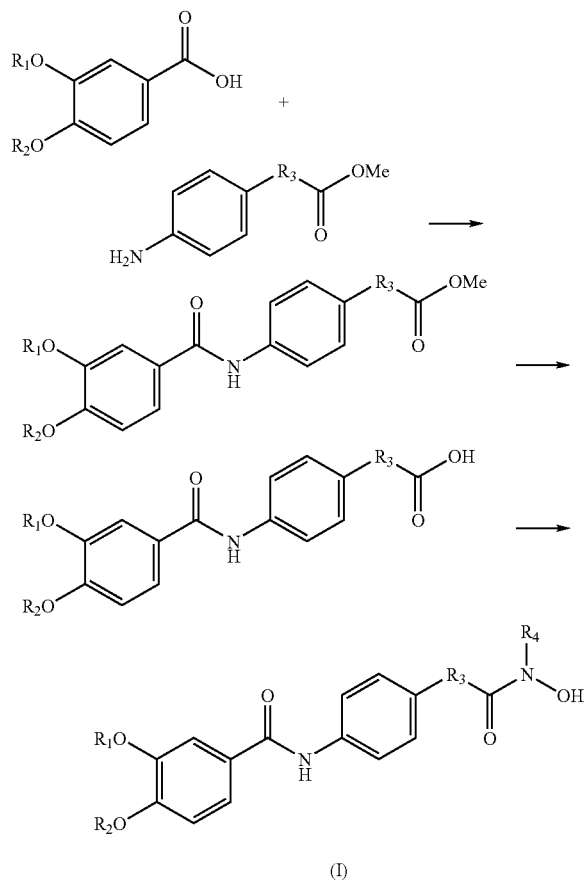

[Reaction Scheme 1]

(I)

wherein, $R_1$ and $R_2$ are an alkyl groups having from 1 to 10 carbon atoms;

$R_3$ is —$(CH)_n$—, wherein n=0 or 1; and $R_4$ is a hydrogen atom or methyl.

Firstly, benzoic acid may be converted to an anhydride by employing ethyl chloroformate in an equivalent ratio of 1.2. A solvent employed herein may be pyridine, N-methylmorpholine and the like. The anhydride may then be reacted with methyl 4-aminobenzoate or 4-aminophenyl acetic acid methylester, to produce a benzamide compound. A solvent employed in this reaction may be pyridine, N-methylmorpholine and the like. Additionally, in a solvent such as N,N-dimethylformamide, methylene chloride, chloroform and the like, the reaction may be performed by further employing trimethylamine, in an equivalent ratio of 1.2 to methyl 4-aminobenzoate or 4-aminophenyl acetic acid methylester. Most preferably, it may be pyridine. Further, the reaction may preferably be performed at a temperature of 10-20° C. At a temperature lower than 10° C., methyl 4-aminobenzoate or 4-aminophenyl acetic acid methylester may remain unreacted and be difficult to withdraw from the product, while, at a temperature higher than 20° C., the anhydride may be hydrolyzed, resulting in a decreased yield of the product.

Subsequently, said methylester of benzamide formed may be hydrolyzed to an acid.

The acid formed may then be converted to an anhydride by employing ethyl chloroformate. Herein, ethyl chloroformate may be employed in an equivalent ratio of 1.2 to the acid. A solvent employed herein may be pyridine, N-methylmorpholine and the like. The said anhydride formed may be reacted with hydroxylamine hydrochloride or N-methyl hydroxylamine hydrochloride, to produce a hydroxamic acid compound. A solvent employed in this reaction may be pyridine, N-methylmorpholine and the like. Additionally, in a solvent such as N,N-dimethylformamide, methylene chloride, chloroform and the like, the reaction may be performed by further employing triethylamine, in an equivalent ratio of 1.2 to hydroxylamine hydrochloride or N-methyl hydroxylamine hydrochloride. Most preferably, it may be pyridine. Further, the reaction may preferably be performed at a temperature of 0-10° C. At a temperature lower than 0° C., hydroxylamine hydrochloride may remain unreacted, resulting in a decreased yield of the product, while at a temperature higher than 10° C., by-products reacting with hydroxyl group of hydroxylamine may be produced and be difficult to withdraw from the product.

Hydroxamic acid derivatives of the formula (1) obtained in said method may include, but are not limited hereto, 1) N-[4-(N-hydroxycarbamoyl)phenyl][3,4-dimethoxyphenyl]carboxyamide, 2) N-[4-(N-hydroxycarbamoyl)phenyl][3,4-diethoxyphenyl]carboxyamide, 3) N-[4-(N-hydroxycarbamoyl)phenyl][3,4-diisopropoxyphenyl]carboxyamide, 4) N-[4-(N-hydroxycarbamoyl)phenyl][3,4-dipropoxyphenyl]carboxyamide, 5) N-[4-(N-hydroxycarbamoyl)phenyl][3,4-dibutoxyphenyl]carboxyamide, 6) N-[4-(N-hydroxycarbamoyl)phenyl][3,4-di-tert-butoxyphenyl]carboxyamide, 7) [4-((3,4-dimethoxyphenyl)carbonyl amino)phenyl]-N-hydroxy-N-methylcarboxyamide, 8) [4-((3,4-diethoxyphenyl)carbonyl amino)phenyl]-N-hydroxy-N-methylcarboxyamide, 9) [4-((3,4-diisopropoxyphenyl)carbonyl amino)phenyl]-N-hydroxy-N-methylcarboxyamide, 10) [4-((3,4-diprorpoxyphenyl)carbonyl amino)phenyl]-N-hydroxy-N-methylcarboxyamide,
11) [4-((3,4-dibutoxyphenyl)carbonyl amino)phenyl]-N-hydroxy-N-methylcarboxyamide,
12) [4-((3,4-di-tert-butoxyphenyl)carbonyl amino)phenyl]-N-hydroxy-N-methylcarboxyamide,
13) N-(4-((hydroxycarbamoyl)methyl)phenyl)-3,4-dimethoxy benzamide,
14) N-(4-((hydroxycarbamoyl)methyl)phenyl)-3,4-diethoxy benzamide,
15) N-(4-((hydroxycarbamoyl)methyl)phenyl)-3,4-diisopropoxy benzamide,
16) N-(4-((hydroxycarbamoyl)methyl)phenyl)-3,4-dipropoxy benzamide,
17) N-(4-(hydroxycarbamoyl)methyl)phenyl)-3,4-dibutoxy benzamide,
18) N-(4-((hydroxycarbamoyl)methyl)phenyl)-3,4-di-tert-butoxy benzamide,
19) N-(4-(N-hydroxy-N-methylcarbonyl)methyl)phenyl)-3,4-dimethoxy benzamide,
20) N-(4-(N-hydroxy-N-methylcarbonyl)methyl)phenyl)-3,4-diethoxy benzamide,
21) N-(4-(N-hydroxy-N-methylcarbonyl)methyl)phenyl)-3,4-diisopropoxy benzamide,
22) N-(4-(N-hydroxy-N-methylcarbonyl)methyl)phenyl)-3,4-dipropoxy benzamide,
23) N-(4-(N-hydroxy-N-methylcarbonyl)methyl)phenyl)-3,4-dibutoxy benzamide,
24) N-(4-(N-hydroxy-N-methylcarbonyl)methyl)phenyl)-3,4-di-tert-butoxy benzamide.

Hydroxamic acid derivatives of the formula (1) obtained in said method have effects as an antioxidant to remove radicals, and simultaneously to promote collagen biosynthesis. In addition, they have effects to contract skin pores. Therefore, hydroxamic acid derivatives of the formula (1) provided by the present invention may be incorporated into medicines or external applications for inhibiting the widening of skin pores as well as for the antioxidation and the improvement of skin wrinkle. In the composition, hydroxamic acid derivatives of the formula (1) can be contained in an amount of 0.0001-20 wt % based on the total weight of the composition.

PREFERRED EMBODIMENT OF THE INVENTION

The methods for preparing hydroxamic acid derivatives according to the present invention are described in more detail by way of the following examples. However, these examples are provided for the purpose of illustration only and should not be construed as limiting the scope of the invention, which will be apparent to one skilled in the art.

EXAMPLE 1

Preparation of N-[4-(N-hydroxycarbamoyl)phenyl] [3,4-dimethoxyphenyl]carboxyamide 20.0 g (0.16 mol) of 3,4-dimethoxy benzoic acid was dissolved in 250 ml of pyridine and then was cooled in an ice bath of 10° C. Thereto, 23.1 g (0.21 mol) of ethyl chloroformate was added dropwise for 30 minutes. The mixture was stirred at room temperature for 2 hours and then filtered to remove salts, to give an anhydride (30.2 g, 0.15 mol). 24.1 g (0.16 mol) of methyl aminobenzoate was dissolved in 250 ml of pyridine and then was cooled in an ice bath of 10° C. Thereto, the anhydride formed in the previous step was added dropwise for 30 minutes. The mixture was stirred for another 2 hours. After distillation of the solvent, the residue was dissolved in 300 ml of ethyl acetate. The ethyl acetate solution was washed with 5% hydrochloric acid and with distilled water, dried over magnesium sulfate, decolorized with active charcoal, and then filtered. The filtrate was dried under reduced pressure, to give methyl(3,4-dimethoxycarbonylamino) benzoate (34.7 g, 85% yield) as a pale yellow solid.

Subsequently, 34.7 g of methyl(3,4-dimethoxycarbonylamino) benzoate was dissolved in 500 ml of methanol, and thereto 50 ml of 10% KOH was added. After stirring for 3 hours, the mixture was neutralized with hydrochloric acid and then filtered, to give an acid compound, (3,4-dimethoxycarbonylamino)benzoic acid (26.2 g, 80% yield).

(3,4-dimethoxycarbonylamino) benzoic acid formed (24.1 g, 0.10 mol) was dissolved in 200 ml of pyridine and then was cooled in an ice bath of 10° C. Thereto, 22.9 g (0.13 mol) of ethyl chloroformate was added dropwise for 30 minutes. The mixture was stirred at room temperature for 2 hours and then filtered to remove salts, to give an anhydride (38.7 g, 0.12 mol).

6.9 g (0.10 mol) of hydroxylamine hydrochloride was dissolved in 100 ml of pyridine and then was cooled in an ice bath of 10° C. Thereto, the anhydride formed in the previous step was added dropwise for 30 minutes. The mixture was stirred for another 2 hours. After distillation of the solvent, the residue was dissolved in 300 ml of ethyl acetate. The ethyl acetate solution was washed with 5% hydrochloric acid and with distilled water, dried over magnesium sulfate, decolorized with active charcoal, and then filtered. The filtrate was dried under reduced pressure, to give a final product, N-[4-(N-hydroxycarbamoyl)phenyl][3,4-dimethoxyphenyl]carboxyamide (16.6 g, 65% yield) as a pale yellow solid.

TLC (in ethyl acetate:hexane=1:1); Rf=0.51;

1H-NMR(DMSO-d6): δ10.84 (s, 1H), 10.01 (s, 1H), 8.84 (s, 1H), 7.10-7.63 (m, 7H), 3.80 (s, 6H).

EXAMPLE 2

Preparation of N-[4-(N-hydroxycarbamoyl)phenyl] [3,4-diethoxyphenyl]carboxyamide Except that 3,4-diethoxy benzoic acid was used instead of 3,4-dimethoxy benzoic acid, the same procedure described in Example 1 was performed to give the title compound (11.9 g, 44% yield) as a pale yellow solid.

TLC (in ethyl acetate:hexane=1:1); Rf=0.53;

1H-NMR(DMSO-d6): δ10.83 (s, 1H), 10.11 (s, 1H), 8.87 (s, 1 H), 7.11-7.60 (m, 7H), 4.20 (m, 4H), 1.27 (t, 6H, J=5.4 Hz).

EXAMPLE 3

Preparation of N-[4-(N-hydroxycarbamoyl)phenyl] [3,4-diisopropoxyphenyl]carboxyamide Except that 3,4-diisopropoxy benzoic acid was used instead of 3,4-dimethoxy benzoic acid, the same procedure described in Example 1 was performed to give the title compound (11.2 g, 43% yield) as a pale yellow solid.

TLC (in ethyl acetate:hexane=1:1); Rf=0.50;
1H-NMR(DMSO-d6): δ10.82 (s, 1H), 10.12 (s, 1H), 8.86 (s, 1H), 7.10-7.64 (m, 7H), 3.41 (m, 2H), 1.24 (d, 12H, J=6.9 Hz).

EXAMPLE 4

Preparation of N-[4-(N-hydroxycarbamoyl)phenyl] [3,4-dipropoxyphenyl]carboxyamide Except that 3,4-dipropoxy benzoic acid was used instead of 3,4-dimethoxy benzoic acid, the same procedure described in Example 1 was performed to give the title compound (11.4 g, 39% yield) as a pale yellow solid.
TLC (in ethyl acetate:hexane=1:4); Rf=0.52;
1H-NMR(DMSO-d6): δ10.82 (s, 1H), 10.13 (s, 1H), 8.86 (s, 1H), 7.10-7.63 (m, 7H), 4.02 (m, 4H), 1.90 (m, 4H), 1.06 (m, 6H).

EXAMPLE 5

Preparation of N-[4-(N-hydroxycarbamoyl)phenyl] [3,4-dibutoxyphenyl]carboxyamide Except that 3,4-dibutoxy benzoic acid was used instead of 3,4-dimethoxy benzoic acid, the same procedure described in Example 1 was performed to give the title compound (12.5 g, 42% yield) as a pale yellow solid.
TLC (in ethyl acetate:hexane=1:1); Rf=0.55;
1H-NMR(DMSO-d6): δ10.80 (s, 1H), 10.13 (s, 1H), 8.84 (s, 1H), 7.11-7.63 (m, 7H), 4.05 (m, 4H), 1.80 (m, 4H), 1.48 (m, 4H), 0.97 (m, 6H).

EXAMPLE 6

Preparation of N-[4-(N-hydroxycarbamoyl)phenyl] [3,4-di-tert-butoxyphenyl]carboxyamide Except that 3,4-di-tert-butoxy benzoic acid was used instead of 3,4-dimethoxy benzoic acid, the same procedure described in Example 1 was performed to give the title compound (14.3 g, 48% yield) as a pale yellow solid.
TLC(in ethyl acetate:hexane=1:1); Rf=0.53;
1H-NMR(DMSO-d6): δ10.83 (s, 1H), 10.11 (s, 1H), 8.87 (s, 1H), 7.11-7.60 (m, 7H), 1.32 (s, 24H).

EXAMPLE 7

Preparation of [4-((3,4-dimethoxyphenyl)carbonylamino)phenyl]-N-hydroxy-N-methyl carboxyamide Except that N-methyl hydroxylamine hydrochloride was used instead of hydroxylamine hydrochloride, the same procedure described in Example 1 was performed to give the title compound (12.8 g, 41% yield) as a pale yellow solid.
TLC (in ethyl acetate:hexane=1:1); Rf=0.52;
1H-NMR(DMSO-d6): δ10.84 (s, 1H), 10.01 (s, 1H), 7.10-7.63 (m, 7H), 3.80 (s, 6H), 3.20 (s, 3H).

EXAMPLE 8

Preparation of [4-((3,4-diethoxyphenyl)carbonylamino)phenyl]-N-hydroxy-N-methyl carboxyamide Except that N-methyl hydroxylamine hydrochloride was used instead of hydroxylamine hydrochloride, the same procedure described in Example 2 was performed to give the title compound (11.8 g, 46% yield) as a pale yellow solid.
TLC (in ethyl acetate:hexane=1:1); Rf=0.53;
1H-NMR(DMSO-d6): δ10.83 (s, 1H), 10.11 (s, 1H), 7.11-7.60 (m, 7H), 4.20 (m, 4H), 3.21 (s, 3H), 1.27 (t, 6H, J=5.4 Hz).

EXAMPLE 9

Preparation of [4-((3,4-diisopropoxyphenyl)carbonylamino)phenyl]-N-hydroxy-N-methyl carboxyamide Except that N-methyl hydroxylamine hydrochloride was used instead of hydroxylamine hydrochloride, the same procedure described in Example 3 was performed to give the title compound (11.9 g, 44% yield) as a pale yellow solid.
TLC (in ethyl acetate:hexane=1:1); Rf=0.50;
1H-NMR(DMSO-d6): δ10.82 (s, 1H), 10.12 (s, 1H), 7.10-7.64 (m, 7H), 3.41 (m, 2H), 3.21 (s, 3H), 1.24 (d, 12H, J=6.9 Hz).

EXAMPLE 10

Preparation of [4-((3,4-dipropoxyphenyl)carbonylamino)phenyl]-N-hydroxy-N-methyl carboxyamide Except that N-methyl hydroxylamine hydrochloride was used instead of hydroxylamine hydrochloride, the same procedure described in Example 4 was performed to give the title compound (11.9 g, 44% yield) as a pale yellow solid.
TLC (in ethyl acetate:hexane=1:1); Rf=0.53;
1H-NMR(DMSO-d6): δ10.82 (s, 1H), 10.13 (s, 1H), 7.10-7.63 (m, 7H), 4.02 (m, 4H), 3.21 (s, 3H), 1.90 (m, 4H), 1.06 (m, 6H).

EXAMPLE 11

Preparation of [4-((3,4-dibutoxyphenyl)carbonylamino)phenyl]-N-hydroxy-N-methylcarboxyamide Except that N-methyl hydroxylamine hydrochloride was used instead of hydroxylamine hydrochloride, the same procedure described in Example 5 was performed to give the title compound (11.9 g, 44% yield) as a pale yellow solid.
TLC (in ethyl acetate:hexane=1:1); Rf=0.54;
1H-NMR(DMSO-d6): δ10.80 (s, 1H), 10.13 (s, 1H), 7.11-7.63 (m, 7H), 4.05 (m, 4H), 3.21 (s, 3H), 1.80 (m, 4H), 1.48 (m, 4H), 0.97 (m, 6H).

EXAMPLE 12

Preparation of [4-((3,4-di-tert-butoxyphenyl)carbonylamino)phenyl]-N-hydroxy-N-methyl carboxyamide Except that N-methyl hydroxylamine hydrochloride was used instead of hydroxylamine hydrochloride, the same procedure described in Example 6 was performed to give the title compound (11.9 g, 44% yield) as a pale yellow solid.
TLC (in ethyl acetate:hexane=1:1); Rf=0.53;
1H-NMR(DMSO-d6): δ10.83 (s, 1H), 10.11 (s, 1H), 7.11-7.60 (m, 7H), 3.20 (s, 3H), 1.32 (s, 24H).

EXAMPLE 13

Preparation of N-(4-((hydroxycarbamoyl)methyl)phenyl)-3,4-dimethoxy benzamide

Except that 4-aminophenyl acetic acid methylester was used instead of methyl amino benzoate, the same procedure described in Example 1 was performed to give the title compound (10.4 g, 42% yield) as a pale yellow solid.

TLC (in ethyl acetate:hexane=1:1); Rf=0.51;
1H-NMR(DMSO-d6): δ10.84 (s, 1H), 10.01 (s, 1H), 8.84 (s, 1H), 7.10-7.63 (m, 7H), 3.80 (s, 6H), 3.12 (s, 2H).

EXAMPLE 14

Preparation of N-(4-((hydroxycarbamyl)methyl)phenyl)-3,4-diethoxy benzamide

Except that 4-aminophenyl acetic acid methylester was used instead of methyl amino benzoate, the same procedure described in Example 2 was performed to give the title compound (10.4 g, 42% yield) as a pale yellow solid.

TLC (in ethyl acetate:hexane=1:1); Rf=0.53;
1H-NMR(DMSO-d6): δ10.83 (s, 1H), 10.10 (s, 1H), 8.87 (s, 1H), 7.11-7.60 (m, 7H), 4.20 (m, 4H), 3.10 (s, 2H), 1.27 (t, 6H, J=5.4 Hz).

EXAMPLE 15

Preparation of N-(4-((hydroxycarbamoyl)methyl)phenyl)-3,4-diisopropoxy benzamide Except that 4-aminophenyl acetic acid methylester was used instead of methyl amino benzoate, the same procedure described in Example 3 was performed to give the title compound (10.4 g, 42% yield) as a pale yellow solid.

TLC (in ethyl acetate:hexane=1:4); Rf=0.50;
1H-NMR(DMSO-d6): δ10.82 (s, 1H), 10.12 (s, 1H), 8.86 (s, 1H), 7.10-7.64 (m, 7H), 3.41 (m, 2H), 3.12 (s, 2H), 1.24 (d, 12H, J=6.9 Hz).

EXAMPLE 16

Preparation of N-(4-((hydroxycarbamoyl)methyl)phenyl)-3,4-dipropoxy benzamide

Except that 4-aminophenyl acetic acid methylester was used instead of methyl amino benzoate, the same procedure described in Example 4 was performed to give the title compound (10.4 g, 42% yield) as a pale yellow solid.

TLC (in ethyl acetate:hexane=1:1); Rf=0.52;
1H-NMR(DMSO-d6): δ10.82 (s, 1H), 10.13 (s, 1H), 8.86 (s, 1H), 7.10-7.63 (m, 7H), 4.02 (m, 4H), 3.12 (s, 2H), 1.90 (m, 4H), 1.06 (m, 6H).

EXAMPLE 17

Preparation of N-(4-((hydroxycarbamoyl)methyl)phenyl)-3,4-dibutoxy benzamide

Except that 4-aminophenyl acetic acid methylester was used instead of methyl amino benzoate, the same procedure described in Example 5 was performed to give the title compound (10.4 g, 42% yield) as a pale yellow solid.

TLC (in ethyl acetate:hexane=1:1); Rf=0.55;
1H-NMR(DMSO-d6): δ10.80 (s, 1H), 10.13 (s, 1H), 8.84 (s, 1H), 7.11-7.63 (m, 7H), 4.05 (m, 4H), 3.12 (s, 2H), 1.80 (m, 4H), 1.48 (m, 4H), 0.97 (m, 6H).

EXAMPLE 18

Preparation of N-(4-((hydroxycarbamoyl)methyl)phenyl)-3,4-di-tert-butoxy benzamide Except that 4-aminophenyl acetic acid methylester was used instead of methyl amino benzoate, the same procedure described in Example 6 was performed to give the title compound (10.4 g, 42% yield) as a pale yellow solid.

TLC (in ethyl acetate:hexane=1:1); Rf=0.53;
1H-NMR(DMSO-d6): δ10.83 (s, 1H), 10.11 (s, 1H), 8.87 (s, 1H), 7.11-7.60 (m, 7H), 3.13 (s, 2H), 1.32 (s, 24H).

EXAMPLE 19

Preparation of N-(4-(N-hydroxy-N-methylcarbonyl)methyl)phenyl)-3,4-dimethoxy benzamide Except that N-methyl hydroxylamine hydrochloride was used instead of hydroxylamine hydrochloride, the same procedure described in Example 13 was performed to give the title compound (12.8 g, 41% yield) as a pale yellow solid.

TLC (in ethyl acetate:hexane=1:1); Rf=0.51;
1H-NMR(DMSO-d6): δ10.84 (s, 1H), 10.01 (s, 1H), 7.10-7.63 (m, 7H), 3.80 (s, 6H), 3.24 (s, 3H), 3.12 (s, 2H).

EXAMPLE 20

Preparation of N-(4-(N-hydroxy-N-methylcarbonyl)methyl)phenyl)-3,4-diethoxy benzamide Except that N-methyl hydroxylamine hydrochloride was used instead of hydroxylamine hydrochloride, the same procedure described in Example 14 was performed to give the title compound (12.8 g, 41% yield) as a pale yellow solid.

TLC (in ethyl acetate:hexane=1:1); Rf=0.53;
1H-NMR(DMSO-d6): δ10.83 (s, 1H), 10.10 (s, 1H), 7.11-7.60 (m, 7H), 4.20 (m, 4H), 3.25 (s, 3H), 3.10 (s, 2H), 1.27 (t, 6H, J=5.4 Hz).

EXAMPLE 21

Preparation of N-(4-(N-hydroxy-N-methylcarbonyl)methyl)phenyl)-3,4-diisopropoxy benzamide Except that N-methyl hydroxylamine hydrochloride was used instead of hydroxylamine hydrochloride, the same procedure described in Example 15 was performed to give the title compound (12.8 g, 41% yield) as a pale yellow solid.

TLC (in ethyl acetate:hexane=1:1); Rf=0.50;
1H-NMR(DMSO-d6): δ10.82 (s, 1H), 10.12 (s, 1H), 7.10-7.64 (m, 7H), 3.41 (m, 2H), 3.24 (s, 3H), 3.12 (s, 2H), 1.24 (d, 12H, J=6.9 Hz).

EXAMPLE 22

Preparation of N-(4-(N-hydroxy-N-methylcarbonyl)methyl)phenyl)-3,4-dipropoxy benzamide Except that N-methyl hydroxylamine hydrochloride was used instead of hydroxylamine hydrochloride, the same procedure described in Example 16 was performed to give the title compound (12.8 g, 41% yield) as a pale yellow solid.

TLC (in ethyl acetate:hexane=1:1); Rf=0.52;
1H-NMR(DMSO-d6): δ10.82 (s, 1H), 10.13 (s, 1H), 7.10-7.63 (m, 7H), 4.02 (m, 4H), 3.21 (s, 3H), 3.12 (s, 2H), 1.90 (m, 4H), 1.06(m, 6H).

EXAMPLE 23

Preparation of N-(4-(N-hydroxy-N-methylcarbonyl) methyl)phenyl)-3,4-dibutoxy benzamide Except that N-methyl hydroxylamine hydrochloride was used instead of hydroxylamine hydrochloride, the same procedure described in Example 17 was performed to give the title compound (12.8 g, 41% yield) as a pale yellow solid.
TLC (in ethyl acetate:hexane=1:1); Rf=0.55;
1H-NMR(DMSO-d6): δ10.80 (s, 1H), 10.13 (s, 1H), 7.11-7.63 (m, 7H), 4.05 (m, 4H), 3.26 (s, 3H), 3.12 (s, 2H), 1.80 (m, 4H), 1.48 (m, 4H), 0.97 (m, 6H).

EXAMPLE 24

Preparation of N-(4-(N-hydroxy-N-methylcarbonyl) methyl)phenyl)-3,4-di-tert-butoxy benzamide Except that N-methyl hydroxylamine hydrochloride was used instead of hydroxylamine hydrochloride, the same procedure described in Example 18 was performed to give the title compound (12.8 g, 41% yield) as a pale yellow solid.
TLC (in ethyl acetate:hexane=1:1); Rf=0.53;
1H-NMR(DMSO-d6): δ10.83 (s, 1H), 10.11 (s, 1H), 7.11-7.60 (m, 7H), 3.24 (s, 3H), 3.13 (s, 2H), 1.32 (s, 24H).

EXPERIMENTAL EXAMPLE 1

Measurement of the Antioxidative Effect

This example illustrates the antioxidative effect of the hydroxamic acid derivatives obtained in Examples 1 to 24, in comparison with tocoperol and EGCG (EpiGalloCatechin Gallate). Human keratinocyte (HaCaT) cell line was divided into $1.0 \times 10^6$ per 60 mm dish, and was cultured for 1 day at 37° C., 5% $CO_2$, using DMEM (FBS 10%) medium containing penicillin/streptomycin, and then was treated with $10^{-4}$ mol % of hydroxamic acid derivatives. The same treatment was performed with tocoperol and EGCG, as positive controls, of the same concentration. The next day, HaCaT cells were treated with 4 mM of BHP (t-butyl hydroperoixe), and were cultured for 4 hours at 37° C., 5% $CO_2$, and the cells were obtained. Lysis of the cells was performed on the cells by way of repeating the freeze/thawing process. The following experiment was performed according to the method presented in the assay kit.

Cabiochem Lipid peroxidation assay kit (Cat. No. 437634) was used as reagent in the present invention, and lipid peroxidation was measured using the principle that peroxidation products of ester which relate to long chain unsaturated fatty acid, such as malondialdehyde (MDA), and 4-hydroxyalkenal, i.e., 4-hydroxy-2(E)-nonenal (4-HNE), react with the reagent to form a stable compound at 586 nm. The results are shown in Table 1.

TABLE 1

| Materials | MDA, HNE |
|---|---|
| Control (without treatment) | 100 |
| t-BHP | 320 |
| Tocoperol | 250 |
| EGCG | 230 |
| Example 1 | 190 |
| Example 2 | 200 |
| Example 3 | 211 |
| Example 4 | 189 |
| Example 5 | 211 |
| Example 6 | 231 |
| Example 7 | 220 |
| Example 8 | 190 |
| Example 9 | 187 |
| Example 10 | 140 |
| Example 11 | 198 |
| Example 12 | 176 |
| Example 13 | 150 |
| Example 14 | 220 |
| Example 15 | 213 |
| Example 16 | 199 |
| Example 17 | 200 |
| Example 18 | 232 |
| Example 19 | 212 |
| Example 20 | 196 |
| Example 21 | 190 |
| Example 22 | 188 |
| Example 23 | 188 |
| Example 24 | 197 |

As can be seen in the above Table 1, hydroxamic acid derivatives obtained in Examples 1 to 24 can be regarded as antioxidants.

EXPERIMENTAL EXAMPLE 2

Effect on Collagen Biosynthesis

This example illustrates the effect of the hydroxamic acid derivatives obtained in Examples 1 to 24 on collagen biosynthesis, in comparison with tocoperol and EGCG.

Human fibroblasts were seeded into 24-well plates at $1 \times 10^5$ cells per well and then cultured to 90% of growth. The fibroblastes were then cultured in serum-free DMEM for 24 hours and treated with $10^{-4}$ M of the hydroxamic acid derivatives of Examples 1-24, tocoperol and EGCG, in serum-free medium, and then incubated in a $CO_2$ incubator for 24 hours.

For each supernatant, procollagen production was measured with procollagen type (I) ELISA kit. The results are shown in Table 2, in which collagen biosynthesis was evaluated as a relative value, in consideration that the value of the control group with no material treated is 100.

TABLE 2

| Materials | Collagen biosynthesis (%) |
|---|---|
| Control group | 100 |
| Tocoperol | 113 |
| EGCG | 120 |
| Example 1 | 123 |
| Example 2 | 131 |
| Example 3 | 122 |
| Example 4 | 111 |
| Example 5 | 121 |
| Example 6 | 135 |
| Example 7 | 111 |
| Example 8 | 112 |
| Example 9 | 123 |
| Example 10 | 126 |
| Example 11 | 121 |

TABLE 2-continued

| Materials | Collagen biosynthesis (%) |
|---|---|
| Example 12 | 123 |
| Example 13 | 111 |
| Example 14 | 121 |
| Example 15 | 134 |
| Example 16 | 131 |
| Example 17 | 123 |
| Example 18 | 122 |
| Example 19 | 142 |
| Example 20 | 123 |
| Example 21 | 121 |
| Example 22 | 122 |
| Example 23 | 123 |
| Example 24 | 131 |

As can be seen in Table 2, hydroxamic acid derivatives obtained in Examples 1 to 24 have an effect on the promotion of collagen biosynthesis.

EXPERIMENTAL EXAMPLE 3

Effect on the Contraction of Skin Pores

This example illustrates the effect of the hydroxamic acid derivatives obtained in Examples 1 to 24 on the contraction of skin pores, in comparison with tocoperol and EGCG.

The compounds of Examples 1-24 were dissolved in solvent (1,3-butylene glycol:ethanol=7:3) to give 1% solution of test samples. To forty-six (46) mice, 0.5 ml of the test sample solution was applied for 1 day, 24 hours later, their back part was biopsied. The epidermis was separated, then soaked in 0.5% acetic acid, then fixed in 10% formalin, and cut vertically by 6 mM. After dying with hematoxylin and eosin, the size of skin pore was measured using Mechanical eyepiece micrometer.

TABLE 3

| Materials | Size of skin pore (mM) |
|---|---|
| Control group | 65 |
| Tocoperol | 64 |
| EGCG | 60 |
| Example 1 | 56 |
| Example 2 | 50 |
| Example 3 | 54 |
| Example 4 | 52 |
| Example 5 | 53 |
| Example 6 | 54 |
| Example 7 | 55 |
| Example 8 | 50 |
| Example 9 | 51 |
| Example 10 | 52 |
| Example 11 | 56 |
| Example 12 | 54 |
| Example 13 | 55 |
| Example 14 | 50 |
| Example 15 | 51 |
| Example 16 | 52 |
| Example 17 | 56 |
| Example 18 | 57 |
| Example 19 | 54 |
| Example 20 | 51 |
| Example 21 | 55 |
| Example 22 | 52 |
| Example 23 | 51 |
| Example 24 | 50 |

As shown in Table 3, the hydroxamic acid derivatives obtained in Examples 1 to 24 were confirmed to contract skin pores effectively, in comparison with tocoperol and EGCG.

Hydroxamic acid derivatives according to the present invention may be incorporated into skin-care external compositions. The present composition may be formulated into, but not limited to, cosmetic compositions such as skin softeners, astringents, nutrient toilet water, nutrient creams, massage creams, essences, eye creams, eye essences, cleansing creams, cleansing foams, cleansing water, packs, powders, body lotions, body creams, body oils, body essences, make-up bases, foundations, hairdyes, shampoos, hair-conditioners and body cleansers; and pharmaceutical compositions such as ointment, gels, creams, patches, and sprays. Also each formulation may further contain bases and additives suitable for the preparation thereof, if necessary, whose kind and amount can be easily selected in this art.

Formulation 1 Nutrient Toilet Water (Milk Lotion)

Nutrient toilet water containing said hydroxamic acid derivatives obtained in Examples 1 to 24 was prepared.

TABLE 4

| Ingredients | Amount (wt %) |
|---|---|
| 1. Distilled water | To 100 |
| 2. Glycerin | 8.0 |
| 3. Butylene glycol | 4.0 |
| 4. Extracts with hyaluronic acid | 5.0 |
| 5. β-glucan | 7.0 |
| 6. Carbomer | 0.1 |
| 7. Hydroxamic acid derivative | q.s. |
| 8. Caprylic/Capric triglyeride | 8.0 |
| 9. Squalane | 5.0 |
| 10. Cetearyl glucoside | 1.5 |
| 11. Sorbitan stearate | 0.4 |
| 12. Cetearyl alcohol | 1.0 |
| 13. Preservative | q.s. |
| 14. Perfume | q.s. |
| 15. Pigments | q.s. |
| 16. Triethanolamine | 0.1 |

Formulation 2 Nutrient Cream

Nutrient cream containing said hydroxamic acid derivatives obtained in Examples 1 to 24 was prepared.

TABLE 5

| Ingredients | Amount (wt %) |
|---|---|
| 1. Distilled water | To 100 |
| 2. Glycerin | 3.0 |
| 3. Butylene glycol | 3.0 |
| 4. Liquid paraffin | 7.0 |
| 5. β-glucan | 7.0 |
| 6. Carbomer | 0.1 |
| 7. Hydroxamic acid derivative | q.s. |
| 8. Caprylic/Capric triglyeride | 3.0 |
| 9. Squalane | 5.0 |
| 10. Cetearyl glucoside | 1.5 |
| 11. Sorbitan stearate | 0.4 |
| 12. Polysorbate 60 | 1.2 |
| 13. Preservative | q.s. |
| 14. Perfume | q.s. |
| 15. Pigments | q.s. |
| 16. Triethanolamine | 0.1 |

Formulation 3 Massage Cream

Massage cream containing said hydroxamic acid derivatives obtained in Examples 1 to 24 was prepared.

TABLE 6

| Ingredients | Amount (wt %) |
|---|---|
| 1. Distilled water | To 100 |
| 2. Glycerin | 8.0 |
| 3. Butylene glycol | 4.0 |

TABLE 6-continued

| Ingredients | Amount (wt %) |
|---|---|
| 4. Liquid paraffin | 45.0 |
| 5. β-glucan | 7.0 |
| 6. Carbomer | 0.1 |
| 7. Hydroxamic acid derivative | q.s. |
| 8. Caprylic/Capric triglyeride | 3.0 |
| 9. Beeswax | 4.0 |
| 10. Cetearyl glucoside | 1.5 |
| 11. Sorbitan sesquioleate | 0.9 |
| 12. Vaseline | 3.0 |
| 13. Preservative | q.s. |
| 14. Perfume | q.s. |
| 15. Pigments | q.s. |
| 16. Paraffin | 1.5 |

Formulation 4 Ointment

Ointment containing said hydroxamic acid derivatives obtained in Examples 1 to 24 was prepared.

TABLE 7

| Ingredients | Amount (wt %) |
|---|---|
| 1. Distilled water | To 100 |
| 2. Glycerin | 8.0 |
| 3. Butylene glycol | 4.0 |
| 4. Liquid paraffin | 15.0 |
| 5. β-glucan | 7.0 |
| 6. Carbomer | 0.1 |
| 7. Hydroxamic acid derivative | q.s. |
| 8. Caprylic/Capric triglyeride | 3.0 |
| 9. Squalane | 1.0 |
| 10. Cetearyl glucoside | 1.5 |
| 11. Sorbitan stearate | 0.4 |
| 12. Cetearyl alcohol | 1.0 |
| 13. Preservative | q.s. |
| 14. Perfume | q.s. |
| 15. Pigments | q.s. |
| 16. Beeswax | 4.0 |

INDUSTRIAL APPLICATION OF THE INVENTION

As described in the above, hydroxamic acid derivatives according to the present invention showed an antioxidation effect and collagen biosynthesis promotion effect, as well as a skin pore contraction effect. As a result, hydroxamic acid derivatives according to the present invention can be incorporated into medicines or skin-care external compositions for improving the widening of skin pore, which is a skin aging phenomenon.

The invention claimed is:

1. A hydroxamic acid derivative represented by the following formula (1):

[Formula 1]

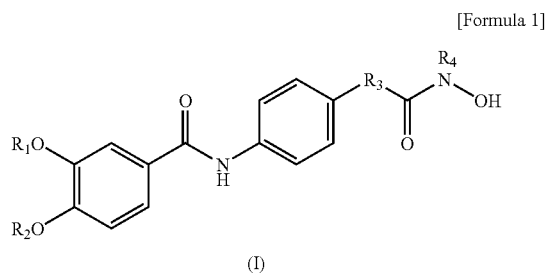

(I)

wherein, $R_1$ and $R_2$ are an alkyl group having from 1 to 10 carbon atoms;

$R_3$ is —$(CH)_n$—, wherein n=0 or 1; and $R_4$ is a hydrogen atom or methyl.

2. The hydroxamic acid derivative according to claim 1, which is selected from the group consisting of:

1) N-[4-(N-hydroxycarbamoyl)phenyl][3,4-dimethoxyphenyl]carboxyamide,
2) N-[4-(N-hydroxycarbamoyl)phenyl][3,4-diethoxyphenyl]carboxyamide,
3) N-[4-(N-hydroxycarbamoyl)phenyl][3,4-diisopropoxyphenyl]carboxyamide,
4) N-[4-(N-hydroxycarbamoyl)phenyl][3,4-dipropoxyphenyl]carboxyamide,
5) N-[4-(N-hydroxycarbamoyl)phenyl][3,4-dibutoxyphenyl]carboxyamide,
6) N-[4-(N-hydroxycarbamoyl)phenyl][3,4-di-tert-butoxyphenyl]carboxyamide,
7) [4-((3,4-dimethoxyphenyl)carbonylamino)phenyl]-N-hydroxy-N-methyl carboxyamide,
8) [4-((3,4-diethoxyphenyl)carbonylamino)phenyl]-N-hydroxy-N-methyl carboxyamide,
9) [4-((3,4-diisopropoxyphenyl)carbonylamino)phenyl]-N-hydroxy-N-methyl carboxyamide,
10) [4-((3,4-dipropoxyphenyl)carbonylamino)phenyl]-N-hydroxy-N-methyl carboxyamide,
11) [4-((3,4-dibutoxyphenyl)carbonylamino)phenyl]-N-hydroxy-N-methyl carboxyamide,
12) [4-((3,4-di-tert-butoxyphenyl)carbonylamino)phenyl]-N-hydroxy-N-methylcarboxyamide,
13) N-(4-((hydroxycarbamoyl)methyl)phenyl)-3,4-dimethoxy benzamide,
14) N-(4-((hydroxycarbamoyl)methyl)phenyl)-3,4-diethoxy benzamide,
15) N-(4-((hydroxycarbamoyl)methyl)phenyl)-3,4-diisopropoxy benzamide,
16) N-(4-((hydroxycarbamoyl)methyl)phenyl)-3,4-dipropoxy benzamide,
17) N-(4-((hydroxycarbamoyl)methyl)phenyl)-3,4-dibutoxy benzamide,
18) N-(4-((hydroxycarbamoyl)methyl)phenyl)-3,4-di-tert-butoxy benzamide,
19) N-(4-(N-hydroxy-N-methylcarbonyl)methyl)phenyl)-3,4-dimethoxy benzamide,
20) N-(4-(N-hydroxy-N-methylcarbonyl)methyl)phenyl)-3,4-diethoxy benzamide,
21) N-(4-(N-hydroxy-N-methylcarbonyl)methyl)phenyl)-3,4-diisopropoxy benzamide,
22) N-(4-(N-hydroxy-N-methylcarbonyl)methyl)phenyl)-3,4-dipropoxy benzamide,
23) N-(4-(N-hydroxy-N-methylcarbonyl)methyl)phenyl)-3,4-dibutoxy benzamide,
24) N-(4-(N-hydroxy-N-methylcarbonyl)methyl)phenyl)-3,4-di-tert-butoxy benzamide.

3. A method for preparing the hydroxamic acid derivative according to claim 1, which comprises the steps of:

1) Reacting 3,4-dialkoxy benzoic acid with methyl 4-aminobenzoate or 4-aminophenyl acetic acid methylester to produce a benzamide compound;
2) Hydrolyzing the methylester of the benzamide compound formed in step 1) to produce an acid; and 3) Reacting said acid with hydroxylamine hydrochloride or N-methyl hydroxylamine hydrochloride to produce a hydroxamic acid derivative.

4. A skin-care external composition for preventing skin aging, containing the hydroxamic acid derivative according to claim 1 as an active ingredient.

5. The composition according to claim 4, wherein said composition is for antioxidation, collagen biosynthesis promotion or skin pore contraction.

6. The composition according to claim 4, wherein said composition is a cosmetic composition.

* * * * *